United States Patent [19]

Reisman

[11] 4,001,595
[45] Jan. 4, 1977

[54] MULTIPLE WAVELENGTH TRANSMISSOMETER

[75] Inventor: Elias Reisman, Orange, Calif.

[73] Assignee: Philco-Ford Corporation (now by change of name Aeronutronic Ford Corporation), Blue Bell, Pa.

[22] Filed: Apr. 23, 1975

[21] Appl. No.: 570,603

[52] U.S. Cl. .............................. 250/575; 250/565; 250/573; 356/102; 356/104; 356/207

[51] Int. Cl.² ................. G01N 21/26; G01N 15/02

[58] Field of Search ............... 250/565, 573, 575; 356/102, 104, 206, 207, 208

[56] References Cited
UNITED STATES PATENTS

| 3,690,772 | 9/1972 | Endl .............................. 356/205 X |
| 3,696,247 | 10/1972 | McIntosh et al. ............. 250/573 X |
| 3,724,951 | 4/1973 | Seelbinder ..................... 356/102 |
| 3,750,883 | 8/1973 | Irving et al. ................... 356/178 X |
| 3,807,876 | 4/1974 | Nakahara et al. ............. 250/575 X |
| 3,820,901 | 6/1974 | Kreuzer ......................... 356/206 X |
| 3,860,818 | 1/1975 | Stalder et al. ................. 250/573 X |

Primary Examiner—Eugene La Roche
Attorney, Agent, or Firm—Robert D. Sanborn

[57] ABSTRACT

A broad band radiant energy beam is passed through a sample region that contains particulate matter. The emergent beam is applied to a plurality of photodetectors, each one of which is made responsive to a different narrow band portion of the beam. The thus obtained electrical signals are applied to a computer which is programmed to process the electrical signals and read out either the size distribution parameters or the mass concentration of the particles in the beam.

5 Claims, 1 Drawing Figure

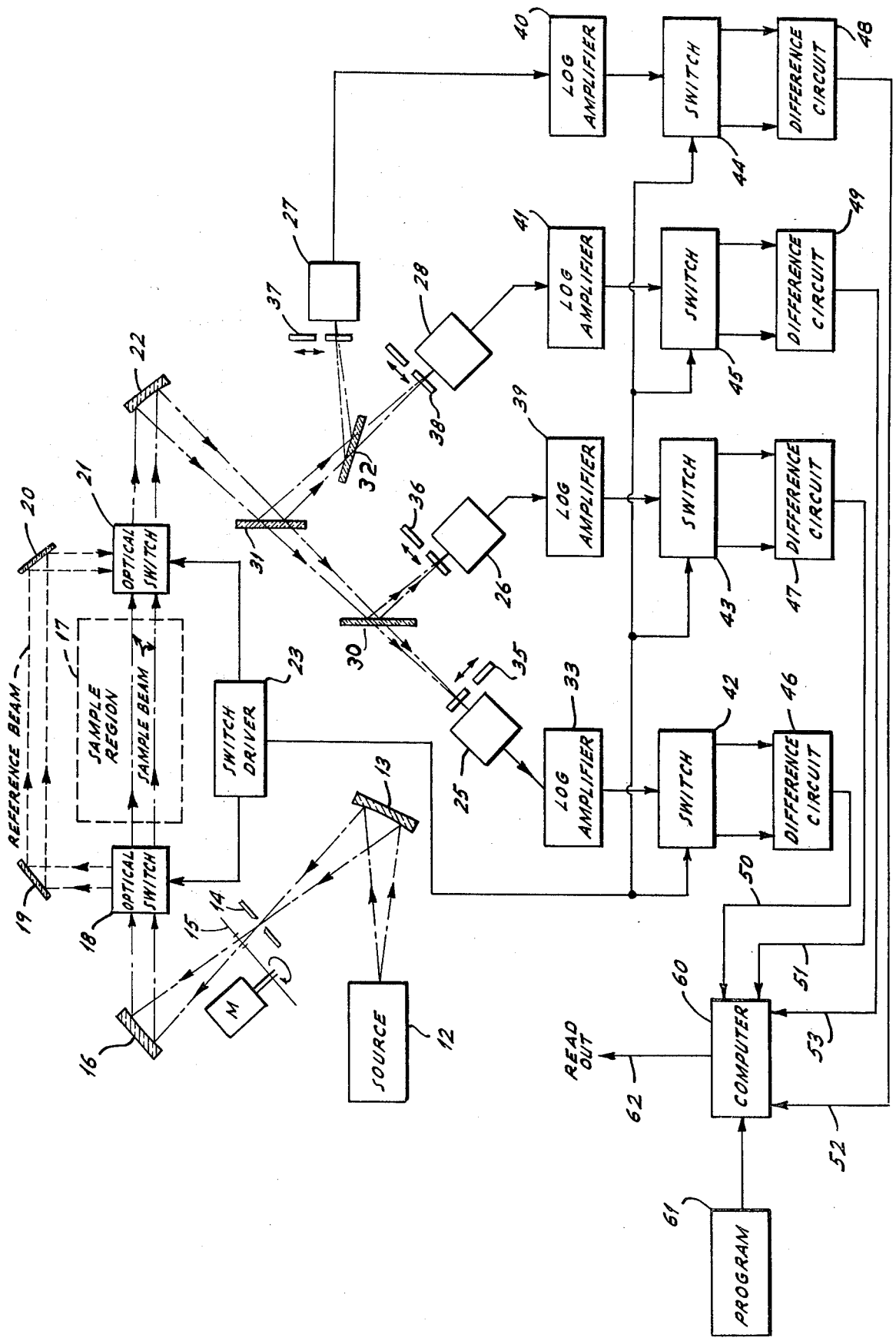

MULTIPLE WAVELENGTH TRANSMISSOMETER

BACKGROUND OF THE INVENTION

It has been known for some time that merely looking at a plume from a smokestack will not yield reliable information on the emission of pollutants. In fact, a stack that appears to be emitting little or no material may in fact be producing great quantities of particulate material in respect to a stack that appears to be emitting copiously. This is due primarily to the size of the emitted particles. If the emitted particles are of a size that interact strongly with visible radiant energy, a relatively small total mass will produce a large optical effect. Also, very small, transparent particles will have much less optical effect than their total mass would lead one to expect. Accordingly, visible radiant energy has proven very unsatisfactory in evaluating emissions.

In general, two methods of measuring particulate effluents have been developed. In the optical method the typical system measures the opacity of a specified path for a specified optical band. In the mechanical method a series of mechanical filters and particle collectors are subjected to the effluent for a period of time. The collectors are carefully weighed before and after and the weight gain noted. The total weight gain is related to the total emission. The plot of weight gain as a function of filter size will yield a particle size distribution, which information is very useful in monitoring a particular process or system.

The mechanical measurements are very time consuming and do not read in real time. Also the readings are on an average value taken over the particle collection period.

The optical systems, while reading in real time and being responsive to rapid fluctuations in emissions, do not yield data on particle size distribution.

SUMMARY OF THE INVENTION

It is an object of the invention to employ optical transmission measurement means to yield both mass concentration and size distribution information of a particle emitting source.

It is a further object of the invention to take transmission measurements through a particulate effluent at a plurality of wavelengths simultaneously and to process the information gained thereby in a digital computer whereby substantially real time data are available on particle size distribution parameters and mass concentration.

These and other objects are achieved in an optical measurement system arranged as follows. Radiation from a broad band optical source is chopped and formed into a beam of finite size which is passed through a sample region containing the particles to be measured. This sample region could be a smokestack or the effluent stack of an industrial process that produces particulate matter. The emergent beam is applied simultaneously to a plurality of photodetectors, each of which is made to respond to a narrow band portion of the spectrum of the beam. The wavelength response of the photodetectors is selected in relation to the size of the particles to be evaluated. In general the spread of the size in particle diameters is matched by the spread in detector wavelength responses. Since a particular process will tend to produce a particle composition, size range, and distribution form that can be established apriori, the real problem is to determine the instantaneous particle size distribution parameters and from them the instantaneous value of mass concentration. This information permits an assessment of the nature of the process, thereby making it possible to evaluate and control the process.

The information produced by the plurality of photodetectors is processed in a digital computer which employs extinction coefficient information on the particles to calculate the size based on relative optical transmission. The computer is programmed in terms of the kind of readout desired and in terms of the nature of the particulate system being analyzed. The readout is then available in terms of total particle mass concentration and/or particle size or mass distribution. The computer can operate fast enough to provide substantially real-time readout and can therefore respond rapidly to fluctuations in particle emission.

BRIEF DESCRIPTION OF THE DRAWING

The single FIGURE of drawing is a block diagram of the preferred embodiment of the invention.

DESCRIPTION OF THE INVENTION

In the drawing, source 12 produces a broad bandwidth of radiant energy in the appropriate portion of the spectrum. For example a Nernst Glower has proved useful in providing adequate radiant energy extending through the visible spectrum and well into the far infrared region. Mirror 13 images source 12 at aperture 14 the size of which is made smaller than the image. Thus aperture 14 is a limiting aperture. Chopper 15, which can be a motor-driven apertured disk, interrupts the radiant energy at a suitable rate. Since the beam is chopped, the electronic portion of the system can operate as an a-c system. This permits greater sensitivity and allows electronic discrimination against spurious radiant energy sources.

Mirror 16, which is focused at the exit of aperture 14, reflects the radiant energy and forms it into a parallel beam as shown. The beam is directed through sample region 17 which is shown in dashed outline. This region is the volume of space wherein the measurement is to be taken. It could be located inside the stack of a furnace or in the effluent outlet of some industrial process in which knowledge of the particulate matter is desired. An optical switch 18 which may take the form of an oscillating mirror alternately allows the beam to pass through sample region 17 and diverts it along the dashed path to mirror 19 which in turn diverts the beam to mirror 20 and then to a second optical switch 21. Switch 21 alternately allows the beam in sample region 17 to pass on to mirror 22 and reflects the beam from mirror 20 toward mirror 22. Switches 18 and 21 are driven in synchronism from driver 23 so that in combination they alternately switch the beam through sample region 17 and then around it. This means that the beam arriving at mirror 22 is alternately exposed to the particulates in region 17 and a reference path around region 17 which path contains no particulate effluent. This arrangement provides for continuous self compensation of the system as will be described hereinafter.

Mirror 22 reflects the parallel beam and focuses it on photodetector 25. Portions of the same beam are diverted by a series of reflectors 30–32 onto photodetectors 26–28. Reflectors 30–32 can be simple non-selective beam splitters or they can be dichroic reflectors selected to divert particular wavelength portions of the beam to the appropriate photodetectors. This latter approach is preferred because it provides greater system sensitivity.

Photodetectors 25–28 are made wavelength selective by locating narrow-band optical filters in front of them. As shown, each photodetector includes a switchable pair of filters 35–38. As indicated by the arrows, one element of each pair can be inserted as desired in front of the associated photodetector. This arrangement gives a four-photodetector system an eight-wavelength capability thereby increasing its versatility.

Photodetectors 25–28 have logarithmic amplifiers 33 and 39–41 connected thereto. Thus the optical signals are converted to their log electrical counterparts. Since the beam is chopped, amplifiers 33 and 39–41 can be a-c amplifiers and, if desired, may be tuned to the chopping frequency. The gain of each of amplifiers 33 and 39–41 is set so that a standard signal level is present at the output when the optical switches are in the state that diverts the beam around region 17. This is the beam reference level and the gain adjustment can be used to compensate for differences in the various detectors and associated optical components. This feature makes the system capable of self calibration.

Amplifiers 33 and 39–41 are connected to electronic switches 42–45. These switches are also driven by driver 23 so that two electrical outputs are present for each amplifier. One output represents the reference beam condition and the other output represents the sample beam condition when it is passed through sample region 17. The switch outputs are connected to difference circuits 46–49 the outputs of which are fed into computer 60.

Since the difference circuit inputs are the logarithmic representations of the reference and sample beam conditions, the outputs on lines 50–53 represent the log of the ratio of optical transmission between reference and sample beams. If there are no particulates in region 17 the reference and sample beams will have the same intensity and the signals on lines 50–53 will be zero because the log of a unity ratio is zero. Since the sample and reference beams employ a common source, optical system and detectors, the system is self compensating.

If particulates are present in region 17 optical attenuation will occur and the signal and reference beams will no longer be equal. For this condition the signals on lines 50–53 will be log representations of the optical beam absorption by particulate matter in sample region 17 at the wavelengths selected by filters 35–38. Thus for any given setting of filters 35-38 computer 60 will receive four electrical signals proportional to the log of the optical absorption in region 17, each one representing a known radiant energy wavelength.

Computer 60, which is run by program 61, compares the electrical inputs with stored data developed for known particulates and provides a readout at 62 of either particle size distribution or particulate mass concentration as determined by program 61. The computational performance of computer 60 is based upon the mathematics that follow.

At any given wavelength, the intensity I of the light beam which has passed through the sample is given by:

$$I(\lambda) = I_o(\lambda) e^{-K(r, \lambda) x} \qquad 1.$$

where $I_0(\lambda)$ is the beam intensity in the absence of particulates, $K(r, \lambda)$ is the extinction coefficient, and $x$ is the path length through the particulates. As indicated by $(\lambda)$ those values are a function of wavelength. The transmission, T, is given by:

$$T = I(\lambda)/I_o(\lambda) = e^{-K(r, \lambda) x} \qquad 2.$$

Taking the negative log yields:

$$-\ln T = \ln I_o - \ln I = K(r, \lambda) x \qquad 3.$$

Since $x$ is fixed at a given site, it is a simple matter to have the computer programs to instruct the computer to divide the input data by $x$ and deal directly with $K(r, \lambda)$. In the actual system shown in the drawing the two beams, I and $I_0$, will be detected and give rise to voltage signals, V and $V_0$. $V=AI$ and $V_o=AI_o$; where A is a proportionality constant. Since both signals are fed through a log amplifier and then differenced, the result is again $Kx$.

$$\ln V_o - \ln V = \ln A + \ln I_o - \ln I = \ln I_o - \ln I = K(r, \lambda) x \qquad 4.$$

Feeding the output of the difference circuit to the computer is the same as feeding $K(r, \lambda)x$ to the computer. The values of the K's are the inputs continuously being fed to the computer, each input giving rise to an evaluation of the mass concentration. The information it needs to make the calculation is stored in the computer. The computer program is designed for the needs of the particular site. This can be better understood by considering the factors which determine K.

For a system of particles of a given material and radius $r$, $$K(r, \lambda) = N_o Q(r, \lambda) \pi r^2 \qquad 5.$$

where $N_0$ is the number of particles per unit volume, $\pi r^2$ is the geometric cross-section, and Q is the extinction efficiency which is a function of $r$ and $\lambda$. The values of Q can be determined from Mie scattering theory and depend on the optical properties of the particle material (i.e., the real and imaginary parts of the refractive index). If the indices of refraction are held constant, then Q is a function of $r/\lambda$. If the indices are known, the values of Q can be found in Mie scattering tables as a function of a parameter, $\alpha$, when:

$$\alpha = 2\pi a/\lambda$$

There is a table for each of a variety of combinations of real and imaginary indices. If the desired pair set is missing, the table can be obtained by interpolation or from Mie calculations. In either event, the relevant information on Q for the particles of interest is stored in the computer. Since the wavelength dependence of K is due to the wavelength dependence of Q (which also depends on $r$), the problem is one of choosing a value of $r$ which gives the best match with the experimentally determined K's (i.e., the inputs to the program). This can be done in a variety of ways which essentially involve calculating theoretical values of $K(\lambda)$ and comparing them to the experimental values. The computer is programmed to judge the quality of the fit by a least square criteria, but other programmed procedures could be used. When the best fit is obtained, the value of r is noted and the mass concentration Mc computed.

$$Mc = N_o \rho \frac{4}{3} \pi r^3 \quad (6)$$

where $4/3\pi r^3$ is the volume of a particle and $\rho$ is the density of the material of which it is composed. A simpler form can be obtained by combining (5) and (6):

$$Mc = \frac{\frac{4}{3} \rho r K(r,\lambda)}{Q(r,\lambda)} \quad (7)$$

In general, Equation (5) is too simple. Emission particles generally occur in a size distribution whose form is characteristic of the type of site. Equation (5) is then replaced by:

$$K(\lambda) = \int_{r_1}^{r_2} N(r) \, Q(r,\lambda) \, \pi r^2 dr \quad (8)$$

where $N(r)$ is the number of particles between $r$ and $r + dr$. Similarly, Equation (7) is replaced by:

$$Mc = \int_{r_1}^{r_2} N(r) \rho \frac{4}{3} \pi r^3 dr \quad (\int_0^\infty N(r) dr = N_o) \quad (9)$$

In analyzing data involving a distribution, the first step is to define a simple distributional form which can be expressed completely by means of a few parameters, and then adjust the parameters to best fit the actual distribution and hence the experimental data. For example, the distribution of mass in certain types of effluents is found to be log normal. This appears to be generally true in processes where the small particulates are formed by abrasion of macroscopic particles; for example, the particulates of asphaltic concrete plants and oil refinery catalytic cracker regenerators. For cases of this nature, the problem is treated as follows:

A generalized normal distribution function looks as follows:

$$I(y') = \frac{1}{\sqrt{2\pi\sigma}} \int_{-\infty}^{y'} e^{\frac{-(y-y_0)^2}{2\sigma^2}} dy \quad (10)$$

where $I(y')$ is the probability that the observable is less than $y'$. The mean value of the distribution is $y' = y_0$ (i.e., $I(y_0) = 0.5$ and $I(\infty) = 1$). The standard deviation is $\sigma$.

An alternate form is the probability density function.

$$P(y) = \frac{1}{\sqrt{2\pi\sigma}} e^{\frac{-(y-y_0)^2}{2\sigma^2}} dy \quad (11)$$

$P(y)$ is the probability of finding the observable between $y$ and $y + dy$.

If the mass of the particle is log normally distributed, then:

$$P(r) = \frac{1}{\sqrt{2\pi\sigma}} e^{\frac{-(\log r/r_0)^2}{2\sigma^2}} \frac{dr}{r} \quad (12)$$

which says that $P(r)$ of the mass lies between $r$ and $r + dr$. The mean of the mass or volume occurs at $r = r_0$. This value of $r$ will be designated $r_v$, the volumetric mean radius. Converting Equations (8) and (9) to the proper distributional form.

$$Mc = \int_0^\infty N(r) \rho \frac{4}{3} \pi r^3 dr = N_o \rho \bar{V} = N_o \rho \frac{4}{3} \pi r_v^3 \quad (13)$$

(i.e., the number of particles times the average mass per particle.) hence, $$\int_0^\infty \frac{\rho n(r) \frac{4}{3} \pi r^3}{Mc} dn = \int_0^\infty \frac{n(r)}{N_o} \frac{r^3}{r_v^3} dn = \int_0^\infty P(r) \frac{r^3}{r_v^3} dr = 1 \quad (14)$$

thus $P(r) \, r^3/r_v^3 \, dr$ is the distribution of the mass, known to be log normal, whence, $$P(r) \frac{r^3}{r_v^3} = \frac{1}{\sigma \sqrt{2\pi}} e^{-\left(\log \frac{r}{r_v}\right)^2 / 2\sigma^2} \frac{1}{r} \quad (15)$$

$$P(r) = \frac{1}{\sigma \sqrt{2\pi}} e^{-\left(\log \frac{r}{r_v}\right)^2 / 2\sigma^2} \frac{r_v^3}{r^3} \quad (16)$$

hence, $$K(\lambda) = \sqrt{\frac{\pi}{2}} \frac{N_o r_v^3}{\sigma} \int_0^\infty e^{-\left(\log \frac{r}{r_v}\right)^2 / 2\sigma} \frac{1}{r^2} Q(n,\lambda) dr \quad (17)$$

$$Mc = \frac{4}{3} \pi r_v^3 \rho N_o \quad (18)$$

The computer is programmed to fit the calculated $K(\lambda)$ to the measured $K(\lambda)$ and selects values for $r$, $\sigma$ and $N_o$ for a best fit. It then calculates Mc using Equation (18).

Another commonly occurring distribution is bimodal. The smoke from a sludge incinerator, for example, contains very fine carbon particles and some very coarse fly ash particles. The size distribution, as determined by sampling, shows that the carbon is between 0.05 and 0.3$\mu$ in radius while the fly ash particles are all greater than 1$\mu$. The carbon constitutes 90 to 95 percent of the mass and an even greater percentage of the opacity. The problem programmed into the computer had the following form:

$$K(\lambda) = K_1(\lambda) + K_2(\lambda) = N_1 \pi r_1^2 Q(\lambda,r) + N_2 \pi r_2^2 Q_2(\lambda,r_2) \quad 19.$$

$$Mc = Mc_1 + Mc_2 = N_1 4/3 \pi r_1^3 \rho_1 + N_2 4/3 \pi r_2^3 \rho_2 \quad 20.$$

where the subscripts 1 and 2 refer to the small and large species, respectively. Equation (19) has four parameters ($N_1$, $N_2$, $r_1$, $r_2$) and hence needs four values of $\lambda$ to effect any solution. The equation is complicated by the dependence of Q on $r$. One simplification that can be used if $K_2$ is not excessive, makes use of the fact that $Q_2$ doesn't vary much at the shorter wavelengths. If we use a second subscript to designate wavelength, then:

$$K_1 - K_2 = K_{11} - K_{12} + K_{21} - K_{22} \qquad 21.$$

The latter term, $(K_{21} - K_{22})$ is exceedingly small since $Q_{21} \approx Q_{22}$. Thus, to excellent approximation:

$$K_1 - K_2 = N_1 \pi r_1^2 (Q_{11} - Q_{12}) \text{ or}$$

$$N_1 r_1^2 = \frac{K_1 - K_2}{\pi(Q_{11} - Q_{12})} \qquad (22)$$

The computer can now be programmed to select value of $N_1$ and $r_1$ compatible with Equation (22) and calculate $K_{11}$, $K_{12}$, $K_{13}$ and $K_{14}$. The residuals $(K_1 - K_{11}, K_2 - K_{12},$ etc.) can then be test-fitted to the $Q_{21}$, $Q_{22}$, etc. for various values of $r$ (since $Q$ is a function of $r$). The fitting desired is as follows: $K_{21}/K_{22} = Q_{21}/Q_{22}$ and $K_{22}/K_{23} = Q_{22}/Q_{23}$, etc. If this can be achieved, then $N_2$ can be calculated and $M_1$ and $M_2$ calculated directly. As a practical matter, when the residuals are too small to be meaningful, it is then best to ignore the large particles, except to note that they constitute some percentage of the mass concentration (e.g., 5%) and make the correction to $M_1$ to find Mc. If the large particles can be neglected or accounted for emperically, then a simpler approach is as follows:

$$K(\lambda) = N_1 \pi r_1^2 Q(\lambda, r) \text{ or } K_1 = N_1 \pi r_1^2 Q_{11} = K_{11}, \text{ etc.}$$

The computer is programmed to select values of $N_1$ and $r_1$ which satisfy $K_1$, and then calculate $K_{12}$ and compare with $K_2$. When $|K_2 - K_{12}|$ is a minimum and $r$ lies in an acceptable domain, it accepts $N_1$ and $r_1$ and calculates Mc.

When $K_1$, $K_2$, $K_3$ and $K_4$ are taken as the average of many runs, the calculated values of Mc fall within a few percent of the average values of Mc as determined by conventional mechanical sampling techniques. When Mc is calculated from the instantaneous values of the K's, a set of points are generated which are completely compatible with the average values (e.g., sampling techniques require averaging for 1 to 2 hours; hence, all experimentally determined values of Mc are averaged).

As shown above particularly in equation (4) the electrical signal desired is the negative logarithm of the photodetector output. The preferred embodiment shown and described provided such a signal on each of lines 50–53 for application to the computer 60. If desired the equipment can be considerably simplified within the scope of the invention by omitting the reference beam section of the instrument in the drawing. This means that optical switches 18 and 21 would not be used nor would mirrors 19 and 20. This would obviate switch driver 23. Also switches 42–45 would be eliminated along with difference circuits 46–49. This would mean that the signals available from log amplifiers 33 and 39–41 would be in the form of the logarithm of the photodetector output. It would then be necessary to perform the additional manipulation on the electrical signal in the computer. Also if desired the amplifiers could be made linear and the computer programmed to take the log thereof. Thus as the equipment in the block diagram is simplified the computer must be complicated to compensate. In the reference beam omission it is to be noted that the system is no longer self compensating. This can be partly offset by using a very stable source 12 of radiant energy and by frequent equipment calibration.

EXAMPLE

A measurement device was constructed along the lines shown in the FIGURE of the drawing except that the reference beam and associated equipment as outlined above were omitted. The reference information was either obtained by independent measurement through the clean stack or by working with sudden opacity changes wherein the reference could be treated as constant and hence cancelled out. The logarithms were taken manually and fed into a time share computer. Stored in the computer were the appropriate Q functions, the most likely distributional form for the particles with the instruction asking for the best least squares fit and the calculations for size and mass concentration.

All radiant energy filter elements were of the narrow band interference type. The elements of filter pair 35 were made responsive at 1.25 and 1.75 microns; filter pair 36, 0.4 and 0.65 microns; filter pair 37, 2.2 and 3.8 microns; and filter pair 38, 9.1 and 12.1 microns. All filters were chosen for operation at wavelengths relatively free of absorption by stack gases. Mirror 31 was dichroic and passed radiant energy below 2 micron while reflecting longer wavelengths. Mirror 30 was dichroic and passed radiant energy longer than 2 microns while reflecting the shorter wavelengths. Mirror 32 was dichroic and passed radiant energy longer than 5 microns while reflecting shorter wavelengths. Photodetector 25 was lead sulphide, photodetector 26 silicon, photodetector 27 lead selenide, and photodetector 28 pyroelectric triglycene sulfate (TGS). Each photodetector had a built in preamplifier (not shown in the drawing) to provide a suitable signal output and impedance level.

Thus the instrument provided optical transmissivity data over the range of red visible light to medium IR. Four specific values out of eight total could be selected by the movable filter arrangement. This range provided good data for particles in the 0.5 to 12 micron range.

The measurement system was used at sites that included oil-fired power generation, a petroleum refinery catalytic cracking unit, a sewage treatment sludge burner, an asphaltic concrete plant, and a secondary brass and lead smelter. For data comparison, the mass concentrations were also measured directly using the Environmental Protection Agency (EPA) particulate sampling train method 5 as published in FR 30 No 247 (Dec. 23, 1971).

The measurement system described provided data that was in good agreement with the EPA method and did so on a continuous read out basis. Thus data were immediately available on particle size distribution and mass concentration, which data ordinarily takes hours to acquire and is then an average value taken over the sampling period.

My invention has been described in terms of the apparatus involved and the theory of the measurement. An operating example of a working system is also set forth. Clearly alternatives and equivalents will occur to a person skilled in the art. For example, four photodetectors are shown in the preferred embodiment with two narrow band filters associated with each. It would be an easy matter to incorporate three or more filters into each photodetector. Also, it would be within the scope of the invention to employ a single filter on each photodetector and then use as many as the designer desires (for example eight). While an optical switch is shown for the reference channel other equivalent means could be employed for referencing. For example, a retro reflector unit placed on the far side of the stack can be used to return the sample beam back through stack to the transmitting unit. Both beams would still contribute to the input of each detector. This could be done by alternately exposing the detector to one, then the other, or by having the two beams chopped at different frequencies, exposing the detector to both and subsequently separating the signals electronically.

Similarly, the electronics can be done in the analogue mode or in the digital mode. For example, the logarithms can be accomplished with log amplifiers, then digitalized and fed into the computer or the output can be digitalized passed through a log converter and then fed into the computer. Numerous variant approaches for stabilization are also obvious. Accordingly, it is intended that my invention be limited only by the following claims.

I claim:

1. A transmissometer for evaluating the particulate matter in a sample region, said transmissometer comprising:
    means for generating radiant energy, said radiant energy characterized as having substantial energy content in at least a plurality of wavelengths extending over a broad portion of the spectrum,
    means for forming said radiant energy into a beam,
    means for passing said beam through said sample region, said beam being selectively attenuated at different ones of said wavelengths as a function of the quantity, nature, and size of the particles present in the portion of the sample region traversed by said beam,
    a plurality of radiant energy detectors,
    means for illuminating said plurality of radiant energy detectors from the beam emerging from said sample region,
    means associated with each detector in said plurality for limiting the spectral response of said detector to a narrow portion of said spectrum, each detector being limited to a different portion of said spectrum,
    means for establishing a plurality of sets of values, each set being representative of the predicted amplitude of signals derived from the outputs of said detectors for a selected size distribution and mass concentration of particulate matter in said sample region, and
    means for comparing signals derived from the outputs of said detectors with selected ones of said sets, thereby to provide an indication of the size distribution and mass concentration of particulate matter in said sample region.

2. The transmissometer of claim 1 further including means for chopping said beam and means for processing the electrical outputs of said detectors as alternating current signals.

3. The transmissometer of claim 2 further including means for alternately passing said beam through said sample region and through a reference path free of the particulates to be measured and means for referencing the electrical outputs of said detectors when said beam is passing through said sample region to the electrical outputs of said detectors when said beam is passing through said reference path.

4. The transmissometer of claim 3 wherein each of said detectors is connected to a separate logarithmic amplifier and the amplifier output present when said beam is being passed through said sample region subtracted from the output present when said beam is being passed through said reference path.

5. A transmissometer for evaluating the particulate matter in a sample region, said transmissometer comprising:
    means for generating radiant energy, said radiant energy characterized as having substantial energy content in at least a plurality of wavelengths extending over a broad portion of the spectrum,
    means for forming said radiant energy into a beam,
    means for alternately passing said beam through said sample region and a reference region, said beam being selectively attenuated at different ones of said wavelengths as a function of the quantity, nature, and size of the particles present in the portion of the sample region traversed by said beam,
    a plurality of radiant energy detectors,
    means for alternately illuminating said plurality of radiant energy detectors from the beam emerging from said sample region and said reference region, respectively,
    means associated with each detector in said plurality for limiting the spectral response of said detector to a narrow portion of said spectrum, each detector being limited to a different portion of said spectrum,
    a plurality of difference circuits, each associated with a corresponding one of said detectors, each of said difference circuits having first and second inputs,
    means including switch means coupling the output of the associated detector alternately to said first and second inputs, respectively, of said difference circuits,
    means for operating said switch means in synchronism with the alternation of said beam whereby the output signal of the associated detector representative of the passage of said beam through said reference region is supplied to said first input of said difference circuit and the output signal of the associated detector representative of the passage of said beam through said sample region is supplied to said second input of said difference circuit,
    means for establishing a plurality of sets of values, each set being representative of the predicted amplitudes of signals at the outputs of said difference circuits for a selected size distribution and mass concentration of particulate matter in said sample region, and
    means for comparing signals derived from the outputs of said difference circuits with selected ones of said sets, thereby to provide an indication of the size distribution and mass concentration of particulate matter in said sample region.

* * * * *